(12) United States Patent
Togawa

(10) Patent No.: US 8,083,719 B2
(45) Date of Patent: Dec. 27, 2011

(54) MEDICINAL-SOLUTION ADMINISTRATION DEVICE

(75) Inventor: Tsuyoshi Togawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/859,821

(22) Filed: Aug. 20, 2010

(65) Prior Publication Data
US 2010/0318032 A1 Dec. 16, 2010

Related U.S. Application Data

(63) Continuation of application No. PCT/JP2009/055689, filed on Mar. 23, 2009.

(30) Foreign Application Priority Data

Mar. 24, 2008 (JP) ................................. 2008-076726

(51) Int. Cl.
*A61M 1/00* (2006.01)

(52) U.S. Cl. ....................................................... 604/151

(58) Field of Classification Search ............... 604/890.1, 604/891.1, 892.1, 131, 151, 183, 154, 155
See application file for complete search history.

(56) References Cited

U.S. PATENT DOCUMENTS

| | | | |
|---|---|---|---|
| 4,545,744 A | 10/1985 | Weber et al. | |
| 5,246,347 A | 9/1993 | Davis | |
| 5,893,842 A | 4/1999 | Imbert | |
| 5,938,640 A * | 8/1999 | Maget et al. | 604/145 |
| 7,407,490 B2 * | 8/2008 | Bendsen et al. | 604/131 |
| 7,828,776 B2 * | 11/2010 | Nemoto et al. | 604/189 |
| 2003/0100864 A1 * | 5/2003 | Bendsen et al. | 604/141 |
| 2003/0135202 A1 | 7/2003 | Harper et al. | |
| 2004/0206362 A1 | 10/2004 | Furuichi et al. | |
| 2005/0029277 A1 | 2/2005 | Tachibana | |
| 2005/0269374 A1 | 12/2005 | Koerner et al. | |
| 2008/0300483 A1 | 12/2008 | Nemoto et al. | |
| 2010/0191223 A1 * | 7/2010 | Togawa | 604/892.1 |
| 2010/0198048 A1 * | 8/2010 | Togawa | 600/411 |

FOREIGN PATENT DOCUMENTS

| | | |
|---|---|---|
| JP | 60-75785 | 4/1985 |
| JP | H2-86551 | 7/1990 |
| JP | 3-504208 | 9/1991 |

(Continued)

OTHER PUBLICATIONS

Theeuwes, F. et al., "Principles of the Design and Operation of Generic Osmotic Pumps for the Delivery of Semisolid or Liquid Drug Formulations", Annals of Biomedical Engineering (1976), vol. 4, No. 4, pp. 343-353.
International Search Report dated Jul. 21, 2009.

*Primary Examiner* — Nicholas Lucchesi
*Assistant Examiner* — Aarti B Berdichevsky
(74) *Attorney, Agent, or Firm* — Scully, Scott, Murphy & Presser, P.C.

(57) ABSTRACT

A medicinal-solution administration device includes a body unit including a drive generator that generates a drive force; and a cartridge unit that is attachable to and detachable from the body unit, the cartridge unit including a medicinal-solution reservoir that accommodates at least a medicinal solution and feeds the medicinal solution toward a medicinal-solution administration side, a power source that causes the drive generator to drive, and a drive transmitter that transmits the drive force generated by the drive generator to the medicinal-solution reservoir to push out the medicinal solution in the medicinal-solution reservoir.

12 Claims, 11 Drawing Sheets

FOREIGN PATENT DOCUMENTS

| | | |
|---|---|---|
| JP | 07-000511 | 1/1995 |
| JP | 2004-321788 | 11/2004 |
| JP | 2005-218865 | 8/2005 |
| WO | WO 03/024385 A1 | 3/2003 |
| WO | WO 2005/123161 A1 | 12/2005 |

* cited by examiner

MEDICINAL-SOLUTION ADMINISTRATION DEVICE

CROSS-REFERENCE TO RELATED APPLICATIONS

This application is a continuation of PCT international application Ser. No. PCT/JP2009/055689 filed on Mar. 23, 2009 which designates the United States, incorporated herein by reference, and which claims the benefit of priority from Japanese Patent Application No. 2008-076726, filed on Mar. 24, 2008, incorporated herein by reference.

BACKGROUND OF THE INVENTION

1. Field of the Invention

The present invention relates to a medicinal-solution administration device that administers a medicinal solution, such as an anticancer agent, continuously and directly to a treatment target, such as a diseased part, over a relatively long period of time.

2. Description of the Related Art

Conventionally, an osmotic pump has been used to administer a medicinal solution of a small amount of about 10 ml in a continuous manner over a relatively long and predetermined period of, for example, about one week (see, Theewes F and Yum S I. Principles of the Design and Operation of Generic Osmotic Pumps for the Delivery of Semisolid or Liquid Drug Formulations. Ann Biomed Eng 1976, 4(4):343-353).

SUMMARY OF THE INVENTION

A medicinal-solution administration device according to an aspect of the invention includes: a body unit including a drive generator that generates a drive force; and a cartridge unit that is attachable to and detachable from the body unit, the cartridge unit including a medicinal-solution reservoir that accommodates at least a medicinal solution and feeds the medicinal solution toward a medicinal-solution administration side, a power source that causes the drive generator to drive, and a drive transmitter that transmits the drive force generated by the drive generator to the medicinal-solution reservoir to push out the medicinal solution in the medicinal-solution reservoir.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a medicinal-solution administration device according to the present invention will be described in detail below with reference to the accompanying drawings. The present invention is not limited to the following embodiments.

First Embodiment

Figure 1:
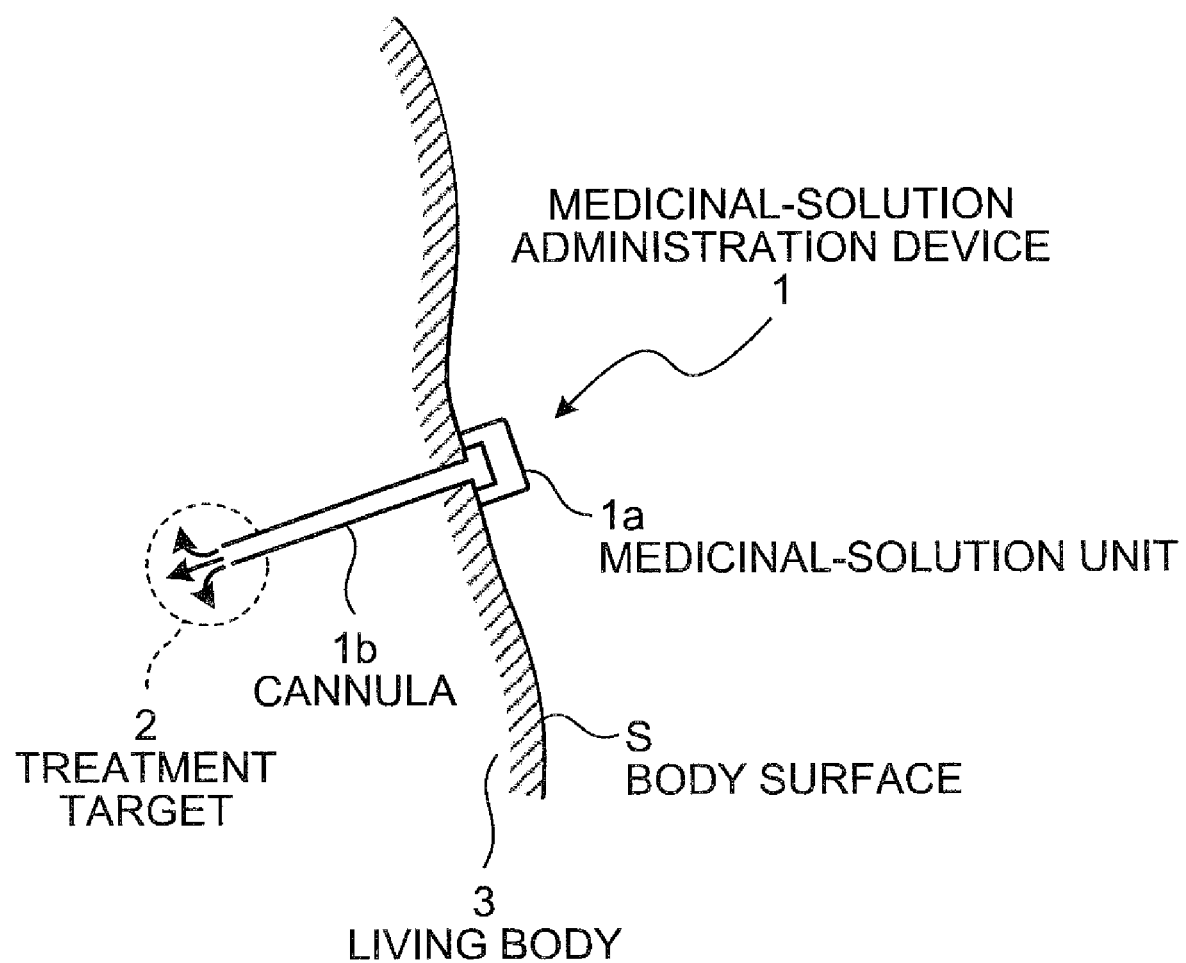
FIG. 1 is a schematic diagram illustrating a state in which a medicinal-solution administration device according to a first embodiment of the present invention is applied to a living body.

FIG. 1 is a diagram illustrating a state in which a medicinal-solution administration device according to a first embodiment of the present invention is applied to a living body such as a human body. In FIG. 1, a medicinal-solution administration device 1 includes a cannula 1b and a medicinal-solution unit 1a. The cannula 1b is configured such that a cannula body having a tip portion for guiding a medicinal solution to a treatment target 2, which is a diseased part such as a cancer, is implanted into a living body 3, and a base portion is placed on a body surface S of the living body 3. The medicinal-solution unit 1a is detachably attached to a base portion 25 of the cannula 1b, and delivers a medicinal solution to the cannula 1b. The medicinal-solution administration device 1 continuously and intensively discharges and administers a medicinal solution of about a few ml, e.g., an anticancer agent such as fluorouracil (5-FU), to the treatment target 2 such as a cancer inside the living body 3 over a relatively long period of, e.g., about one week.

Figure 2:
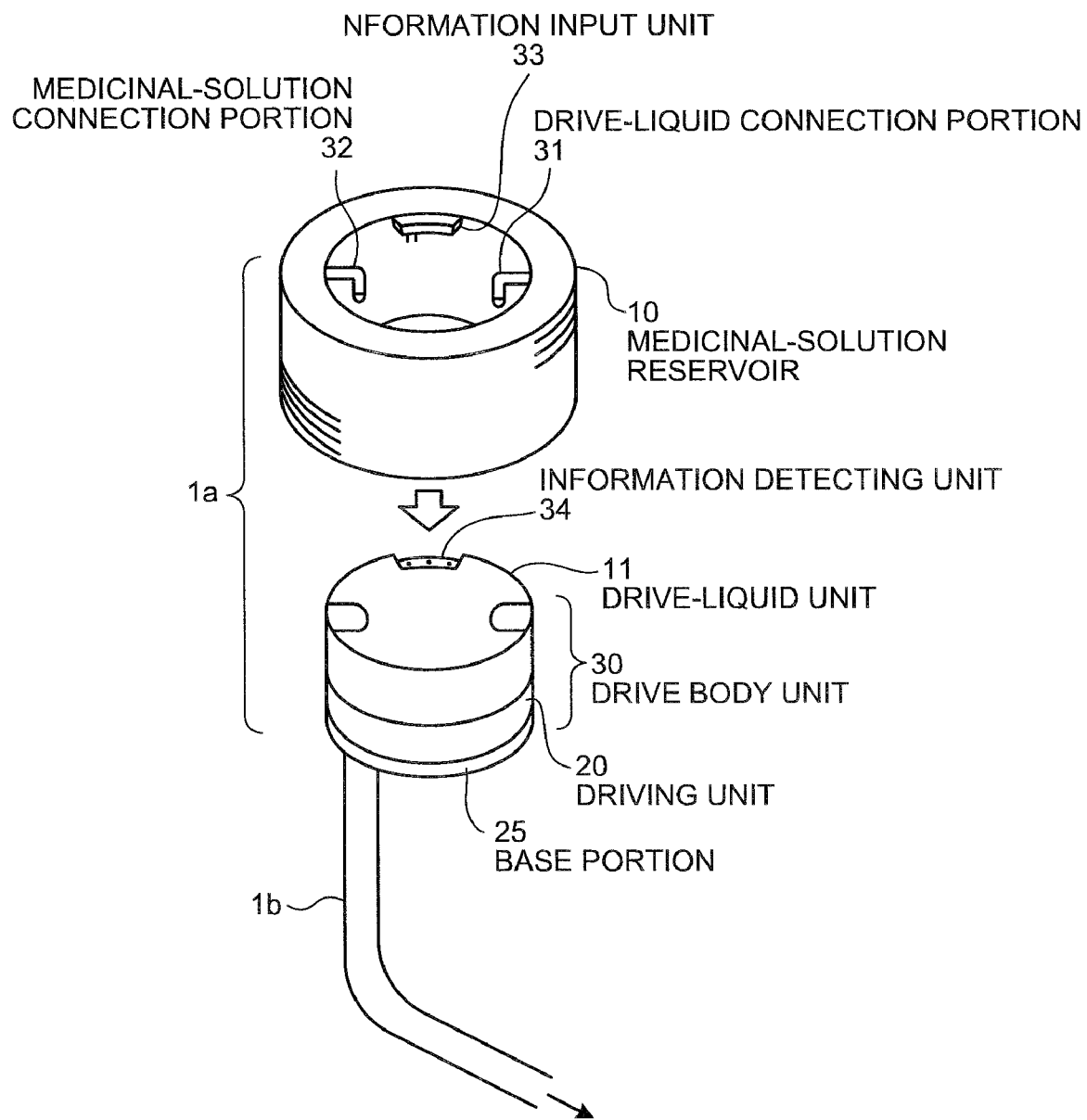
FIG. 2 is an exploded perspective view of the medicinal-solution administration device illustrated in FIG. 1.
Figure 3:
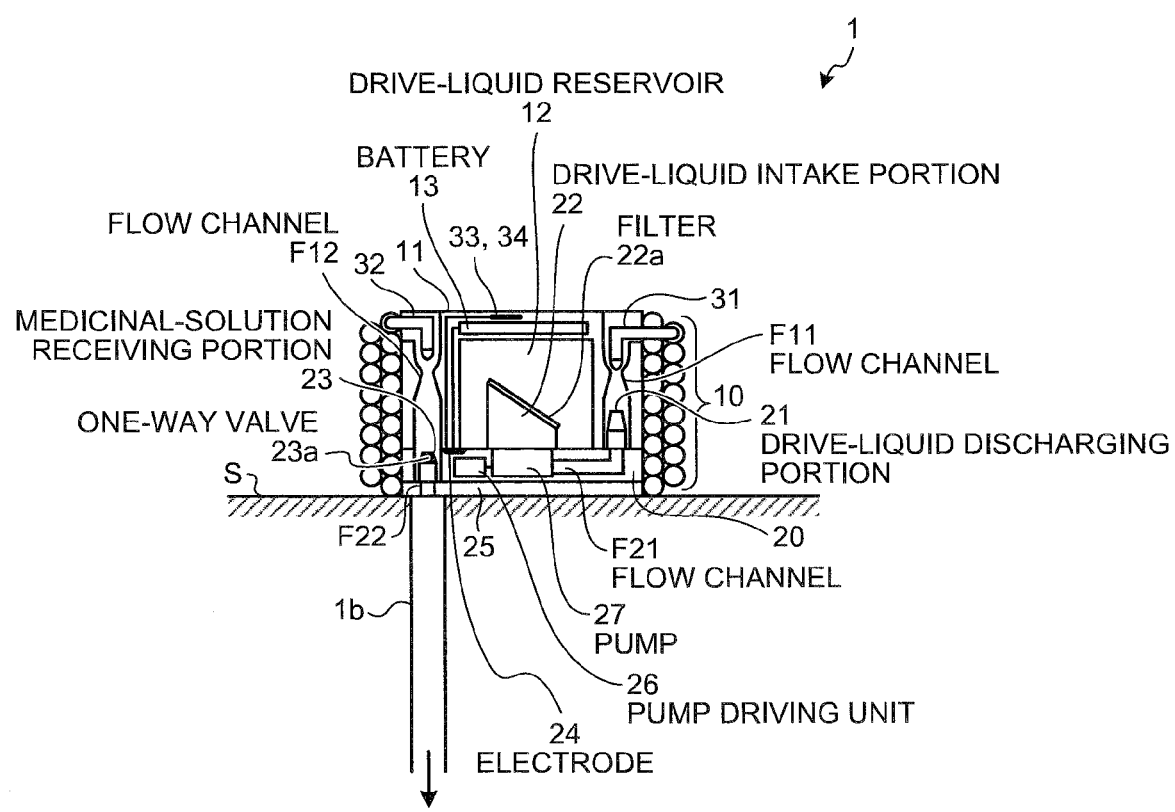
FIG. 3 is a cross-sectional view of the medicinal-solution administration device illustrated in FIG. 1.
Figure 4:
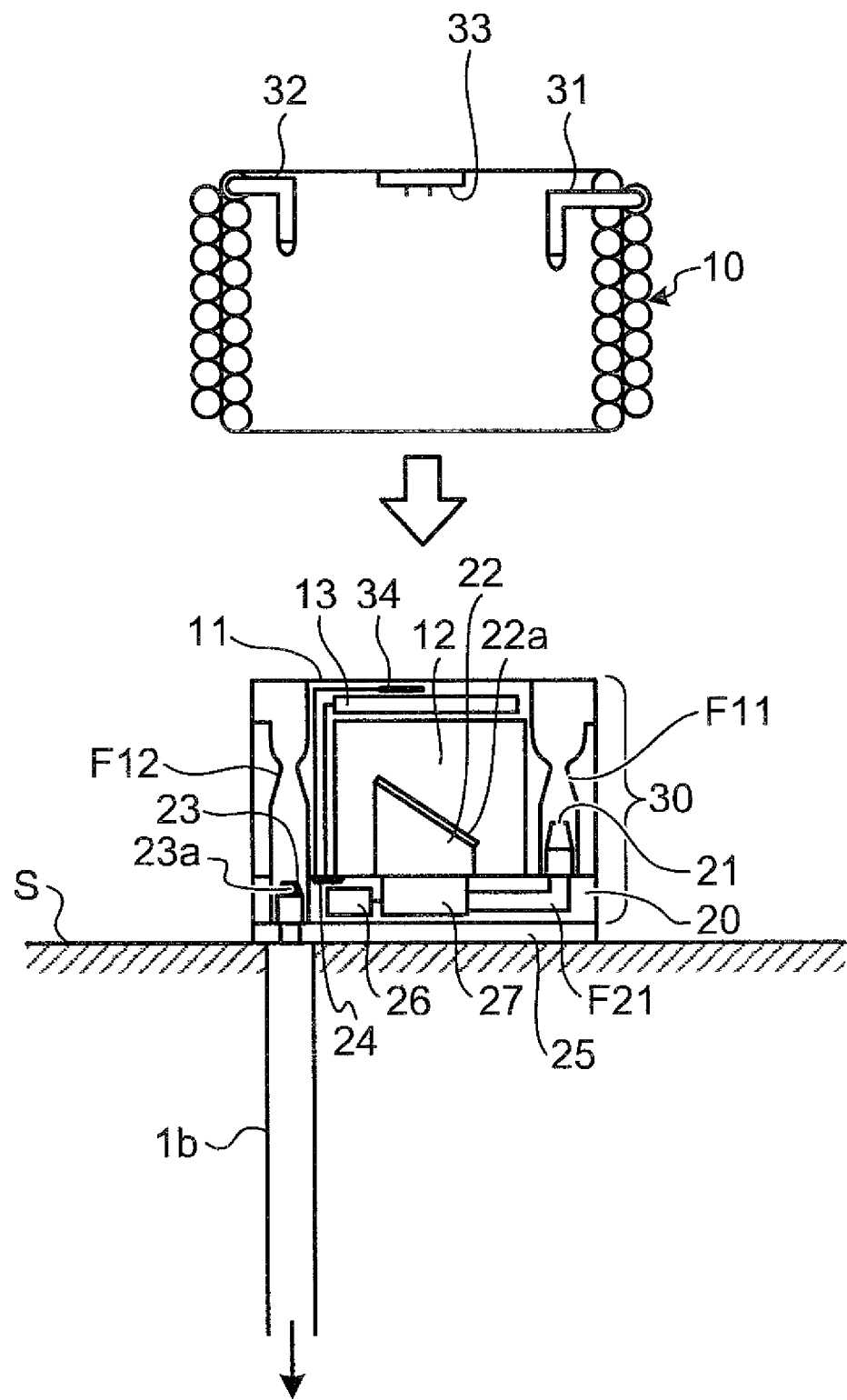
FIG. 4 is an exploded cross-sectional view of the medicinal-solution administration device illustrated in FIG. 1.

FIG. 2 is an exploded perspective view of the medicinal-solution administration device 1 illustrated in FIG. 1. FIG. 3 is a cross-sectional view of the medicinal-solution administration device 1 illustrated in FIG. 1. FIG. 4 is an exploded cross-sectional view of the medicinal-solution administration device 1 illustrated in FIG. 1. In FIGS. 2 to 4, the medicinal-solution administration device 1 mainly includes the medicinal-solution unit 1a and the cannula 1b as described above. The medicinal-solution unit 1a includes a medicinal-solution reservoir 10, which is substantially cylindrical, and a drive body unit 30 (driver) covered by a casing, which is substantially cylindrical. The medicinal-solution reservoir 10 is formed such that a pipe in the form of either a loop or a coil, which is a continuous loop, is tightly and doubly wound, and a medicinal solution is accommodated in the pipe. The drive body unit 30 includes a drive-liquid unit 11, a driving unit 20, and the base portion 25. The drive-liquid unit 11 is positioned in an internal space of the medicinal-solution reservoir 10 in the form of a cylinder, is covered by a casing in the form of a substantial cylinder, and includes at least a drive-liquid reservoir 12 accommodating a drive liquid (drive transmitter) for pushing out the medicinal solution. The driving unit 20 includes a pump 27 (drive generator). The pump 27 is positioned in an internal space of the medicinal-solution reservoir 10, and arranged adjacent to the drive-liquid unit 11. The pump 27 is realized by, for example, an electro-osmotic pump that pushes out a drive liquid for pushing out the medicinal solution.

The drive-liquid unit 11, the driving unit 20, and the base portion 25 are substantially columnar, and integrally assembled in this order toward the cannula 1b side along an axial direction of a cylindrical internal space formed by the medicinal-solution reservoir 10. The drive body unit 30 functions as a driver that pushes out a medicinal solution in the medicinal-solution reservoir 10. The medicinal-solution reservoir 10 is detachably attached to the drive body unit 30.

When assembled, the drive-liquid reservoir 12 in the drive-liquid unit 11 is connected to the pump 27 of the driving unit 20 through a drive-liquid intake portion 22 arranged in the substantial center of the driving unit 20. At an intake of the drive-liquid intake portion 22 is arranged a filter 22a for preventing particles from being mixed into the drive liquid. An output side of the pump 27 in the driving unit 20 is connected to an input side of the medicinal-solution reservoir 10 via a flow channel F21 in the driving unit 20, a drive-liquid discharging portion 21, and a flow channel F11 in the drive-liquid unit 11. In FIG. 3, the pipe of the medicinal-solution reservoir 10 runs from an upper outer side on the upper right→a lower outer side→a lower inner side→an upper inner side on the upper left. A medicinal solution in the medicinal-solution reservoir 10 is pushed out by the drive liquid introduced into the medicinal-solution reservoir 10. The pushed-out medicinal solution is delivered to the cannula 1b via a flow channel F12 in the drive body unit 30, and a medicinal-solution receiving portion 23 and a flow channel F22 in the base portion 25. The medicinal-solution receiving portion 23 and the flow channel F12 are connected to each other at the time of assembling. In the medicinal-solution receiving portion 23 is arranged a one-way valve 23a functioning as a check valve that prevents, when the medicinal-solution reservoir 10 is detached, back-flow of a medicinal solution from the living body 3 side due to high pressure inside the body.

A pump driving unit 26 that controls drive of the pump 27 is arranged in the driving unit 20. A battery 13 is mounted on the top of the drive-liquid unit 11. An electrode 24 is arranged on a joint surface of the driving unit 20, on which the drive-liquid unit 11 is joined. Energy supplied by the battery 13 is supplied to at least the pump driving unit 26 via the electrode 24.

As described above, the pump 27 realized by the electro-osmotic pump that pushes out the drive liquid for pushing out the medicinal solution is arranged between the drive-liquid reservoir 12 and the medicinal-solution reservoir 10. The operating principle of the electro-osmotic pump is such that the surfaces inside fine pores of an electro-osmotic material (porous material) are charged negatively, excessive positive ions are present in the vicinity of the surfaces, and the positive ions are caused to move because they are subjected to a force due to an electric field applied from the outside, so that the drive liquid is caused to flow, whereby the drive liquid is discharged. Therefore, a discharge amount of the drive liquid can be changed by changing the intensity of the electric field. The drive-liquid unit has a replenishing unit not illustrated, so that the drive liquid can be replenished from the outside via the replenishing unit. It is desirable to use ultrapure water and the like as the drive liquid.

The pump 27 obtains the drive liquid from the drive-liquid reservoir 12, and pushes out the drive liquid to the medicinal-solution reservoir 10 to thereby indirectly pushes the medicinal solution to the cannula 1b outside the medicinal-solution reservoir 10. An air layer or oil is filled between the drive liquid and the medicinal solution to separate the drive liquid and the medicinal solution from each other in order to prevent mixture.

The above-mentioned medicinal-solution reservoir 10 is detachably attached to the drive body unit 30. The medicinal-solution reservoir 10 and the drive body unit 30 are combined with each other by a drive-liquid connection portion 31 and a medicinal-solution connection portion 32 that combine an inlet and an outlet of the medicinal-solution reservoir 10, and an inner wall of the medicinal-solution reservoir 10 functions as a guide for attachment to and detachment from the drive body unit 30. The drive-liquid connection portion 31 on the medicinal-solution reservoir 10 side is detachably connected to the flow channel F11 of the drive body unit 30. The medicinal-solution connection portion 32 on the medicinal-solution reservoir 10 side is detachably connected to the flow channel F12 of the drive body unit 30. The medicinal solution in the medicinal-solution reservoir 10 is consumable supplies, and is replaced by replacing the medicinal-solution reservoir 10 as a whole as an integrated cartridge. In particular, even when the cannula 1b is implanted into the living body 3, it is possible to replace only the medicinal-solution reservoir 10, so that the medicinal solution can be administered continuously.

The medicinal-solution reservoir 10 includes an information input unit 33 for inputting medicinal-solution administration information, which is medicinal-solution administration information related to an administration amount of the medicinal solution and is specific to the medicinal-solution reservoir. The drive body unit 30 includes an information detecting unit 34 that detects the medicinal-solution administration information input by the information input unit 33. The information input unit 33 includes three protrusions for representing the medicinal-solution administration information on the accommodated medicinal solution by three-bit information, and is arranged on the internal space side of the medicinal-solution reservoir 10. Examples of the medicinal-solution administration information include, but not limited to, a standard administration amount of the medicinal solution per unit time (ml/h), a maximum administration amount, and an effective amount of the medicinal solution. Furthermore, the information input unit 33 may be embodied in various forms other than the three protrusions. On the other hand, the information detecting unit 34 includes detecting portions for detecting the three-bit information corresponding to the three protrusions. When the medicinal-solution reservoir 10 is attached to the drive body unit 30, respective bit-corresponding positions of the information input unit 33 and the information detecting unit 34 are combined with each other by using the medicinal-solution connection portion 32 and the drive-liquid connection portion 31 as positioning mechanisms in circumferential directions.

The medicinal-solution administration information represents information on the administration amount of the medicinal solution by three bits, and the information detected by the information detecting unit 34 is input to the pump driving unit 26 via the electrode 24. The pump driving unit 26 controls the pump 27 based on the input medicinal-solution administration information to thereby control the administration amount of the medicinal solution. The medicinal-solution administration information may be information indicating time profile information related to the administration amount of the medicinal solution. In this case, it is preferable that the pump driving unit 26 stores detailed medicinal-solution administration amount information corresponding to the bit information being the input medicinal-solution administration amount information. Although the above-mentioned three bits indicate the eight types of medicinal-solution administration information, the present invention is not limited to this example. It is possible to include an information input unit and an information detecting unit for handling the increased number of bits. Furthermore, it is possible to input the medicinal-solution administration information by using a configuration in which the mounting position of the medicinal-solution connection portion 32 or the drive-liquid connection portion 31 is adjusted to the protrusion position (bit position) of the information input unit 33. While the information input unit 33 and the information detecting unit 34 described above are physically contacted with each other to input the medicinal-solution administration information, it is possible to input the medicinal-solution administration information by electrical contact. Furthermore, it is possible to arrange a memory chip or a bit switch for storing the bit information representing the medicinal-solution administration information onto the medicinal-solution reservoir 10 side and to cause the pump driving unit 26 to read the bit information by electrical contact when the medicinal-solution reservoir 10 is attached. Namely, any configurations may be applied as long as the medicinal-solution administration information can be input by attaching the medicinal-solution reservoir 10. Thus, according to the embodiment, it is possible to replace the medicinal solution and cope with a new required amount when a type of the medicinal solution is changed, in contrast to a conventional osmotic pump that has difficulty with replacement of the medicinal solution. Furthermore, as described above, because the medicinal-solution reservoir 10 is provided with the medicinal-solution administration information, it is possible to prevent a failure to set the amount caused by a human error when the medicinal solution is replaced.

According to the first embodiment, the medicinal-solution reservoir 10 is detachably attached to the drive body unit 30, so that it is possible to replace the medicinal-solution reservoir 10. Therefore, even with a medicinal-solution administration device having the drive body unit 30 that variably controls the administration amount of the medicinal solution by using a drive liquid, it is possible to easily replace the medicinal solution as consumable supplies.

Second Embodiment

Next, a second embodiment of the present invention is explained. In the embodiment described above, only the medicinal-solution reservoir 10 is detachable. However, in the second embodiment, the medicinal-solution reservoir 10 and the drive-liquid unit 11 are integrated with each other so that not only the medicinal solution but also the drive liquid can be replaced together with the medicinal solution. In other words, the drive-liquid unit 11 is arranged not on the drive body unit 30 (driver) side but on the medicinal-solution reservoir 10 side. The medicinal-solution reservoir 10 and the drive-liquid unit 11 integrated with each other are detachably attached to the drive body unit 30.

Figure 5:
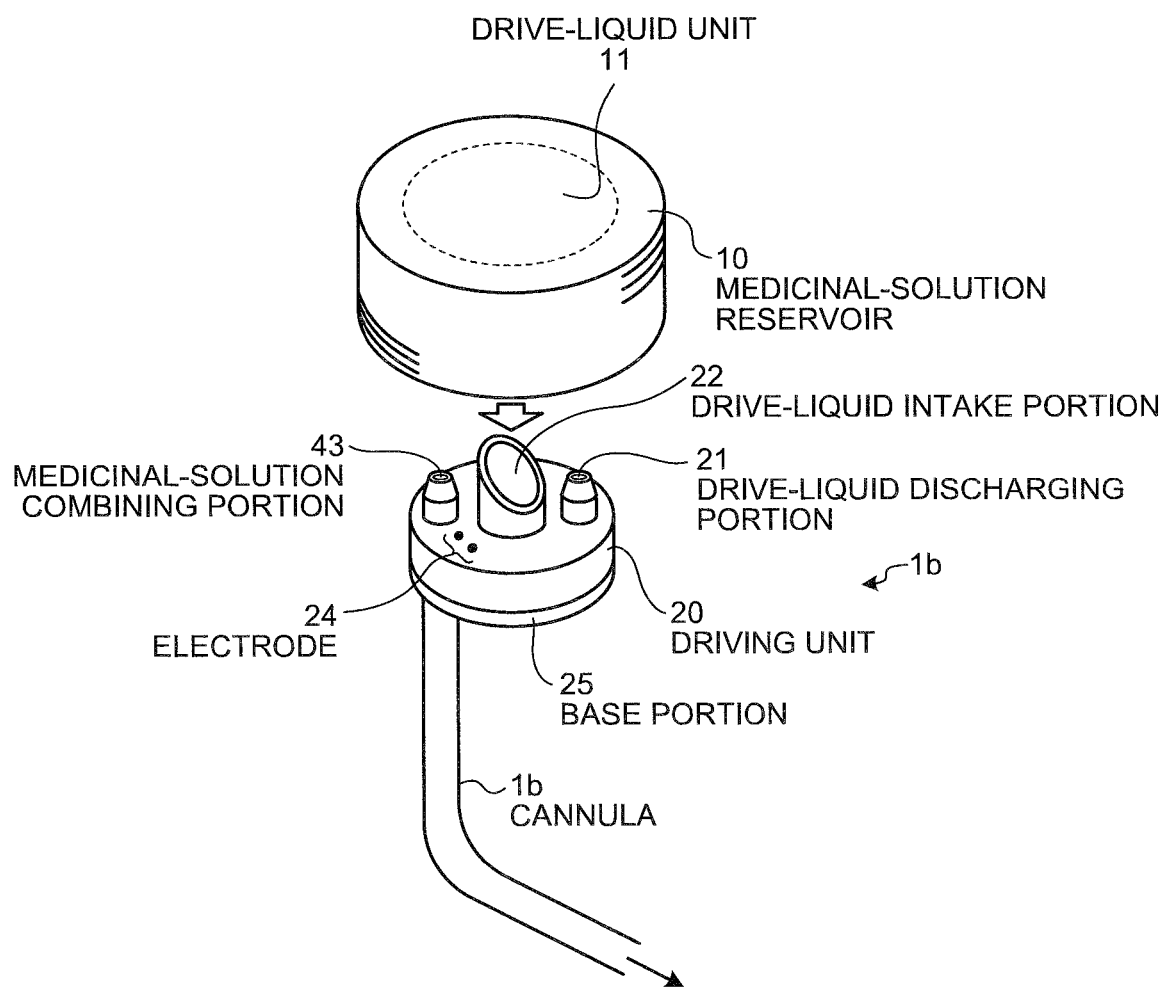
FIG. 5 is an exploded perspective view of a medicinal-solution administration device according to a second embodiment of the present invention.
Figure 6:
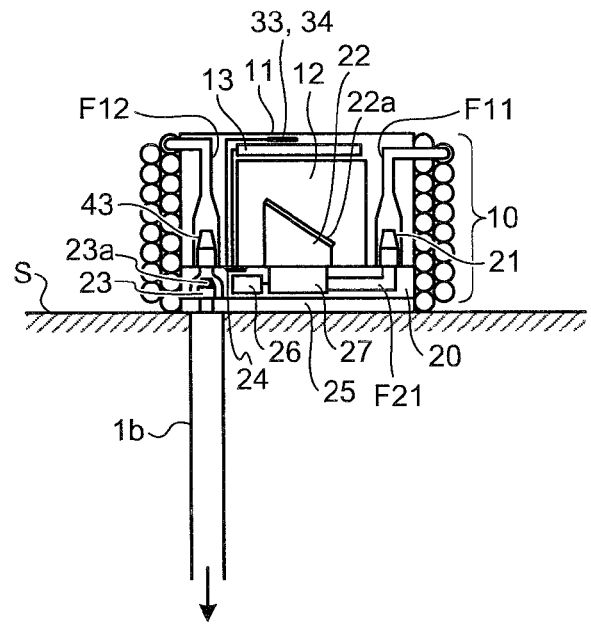
FIG. 6 is a cross-sectional view of the medicinal-solution administration device illustrated in FIG. 5.
Figure 7:
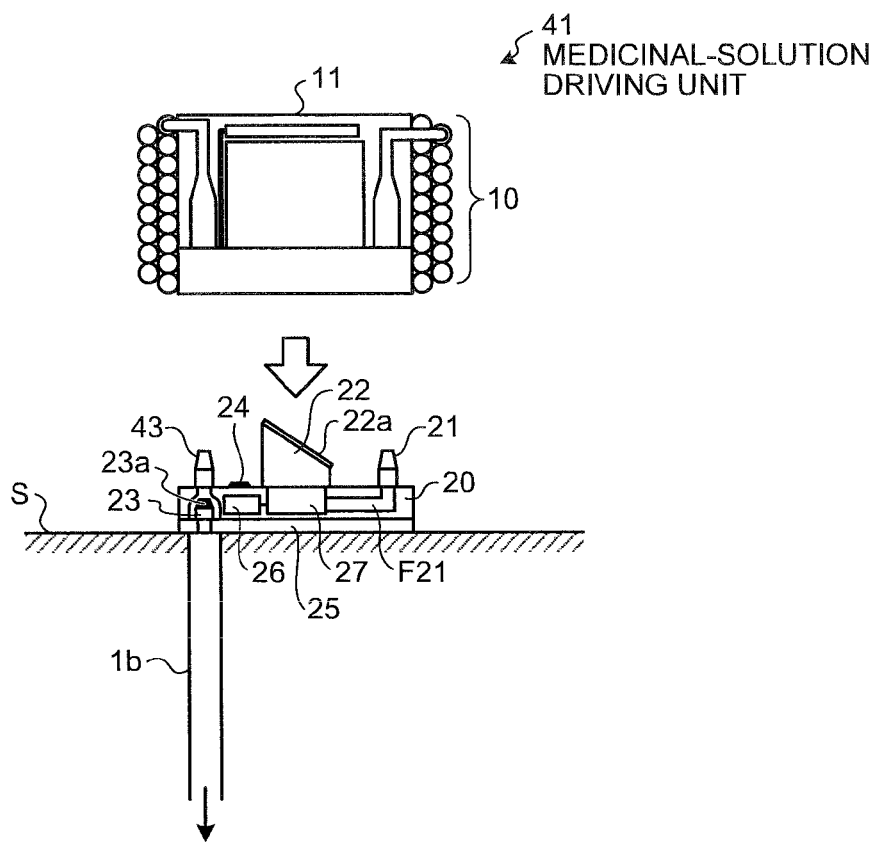
FIG. 7 is an exploded cross-sectional view of the medicinal-solution administration device illustrated in FIG. 5.

FIG. 5 is an exploded perspective view of a medicinal-solution administration device according to the second embodiment of the present invention. FIG. 6 is a cross-sectional view of the medicinal-solution administration device illustrated in FIG. 5. FIG. 7 is an exploded cross-sectional view of the medicinal-solution administration device illustrated in FIG. 5. In FIGS. 5 to 7, in the medicinal-solution administration device, a medicinal-solution combining portion 43, which is inserted in the flow channel F12, is provided on the driving unit 20 side so that the drive-liquid unit 11 and the driving unit 20 can be detached from each other. Furthermore, the medicinal-solution reservoir 10 and the drive-liquid unit 11 are integrated with each other. In the second embodiment, the medicinal-solution connection portion 32 and the drive-liquid connection portion 31 described in the first embodiment are removed, and the inlet and the outlet of the medicinal-solution reservoir 10 are directly connected to the flow channels F11 and F12, respectively. Other configurations are the same as those of the first embodiment.

A medicinal-solution driving unit 41 that includes the medicinal-solution reservoir 10 and the drive-liquid unit 11 integrated with each other is detachably attached to the driving unit 20. The medicinal-solution administration information similar to that of the first embodiment is set when the medicinal-solution driving unit 41 is integrally formed, and is input to the driving unit 20 side via the electrode 24. It is of course possible to arrange a mechanism corresponding to the information input unit between the drive-liquid unit 11 and the driving unit 20, and a mechanism corresponding to the information detecting unit between the medicinal-solution reservoir 10 and the driving unit 20.

According to the second embodiment, because the medicinal-solution reservoir 10 and the drive-liquid unit 11 are integrated with each other and they are detachable, it is possible to easily replace consumable supplies, such as the medicinal solution in the medicinal-solution reservoir 10, the drive liquid in the drive-liquid unit 11, and the battery 13, in an integrated manner.

Third Embodiment

Next, a third embodiment of the present invention is explained. In the first embodiment described above, only the medicinal-solution reservoir 10 is detachable, and, in the second embodiment described above, the medicinal-solution reservoir 10 and the drive-liquid unit 11 are detachable. In contrast, in the third embodiment, the medicinal-solution reservoir 10 and the drive-liquid unit 11 are formed such that they are independently detachable.

Figure 8:
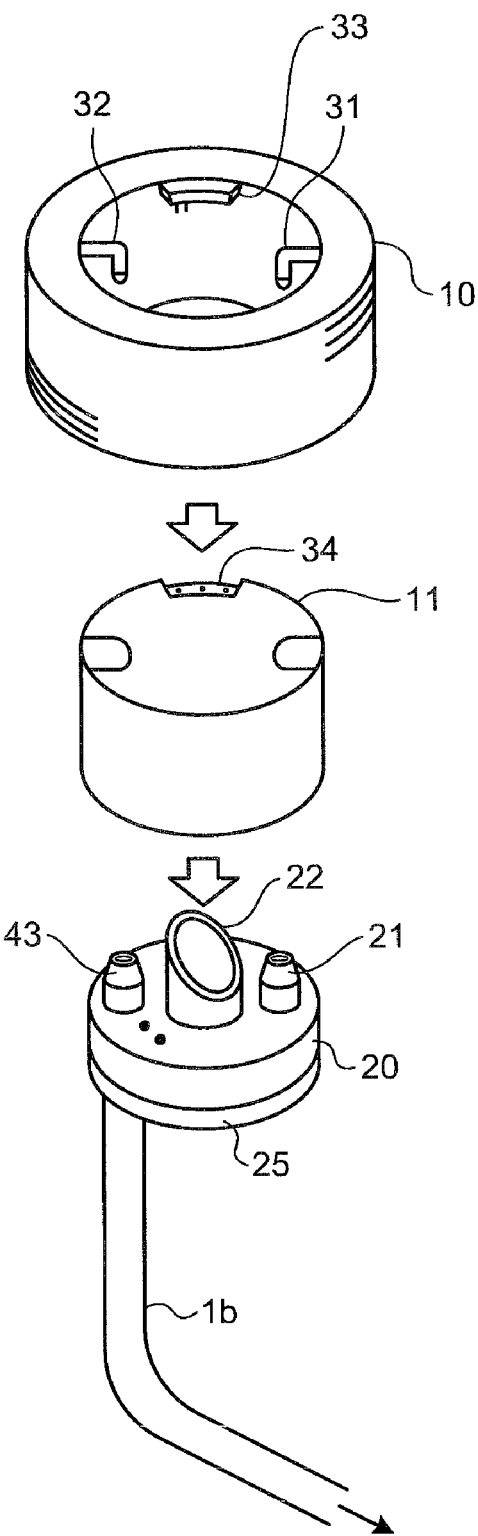
FIG. 8 is an exploded perspective view of a medicinal-solution administration device according to a third embodiment of the present invention.
Figure 9:
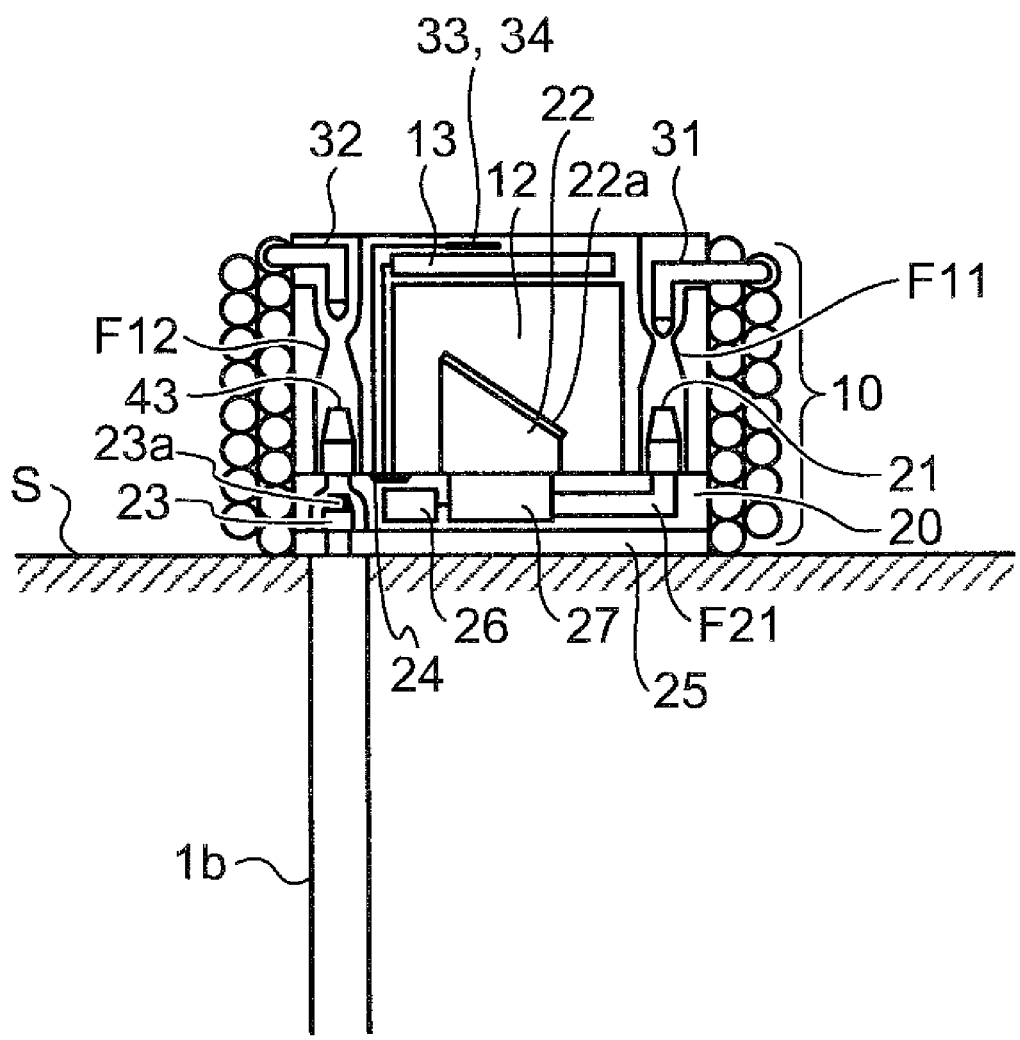
FIG. 9 is a cross-sectional view of the medicinal-solution administration device illustrated in FIG. 8.
Figure 10:
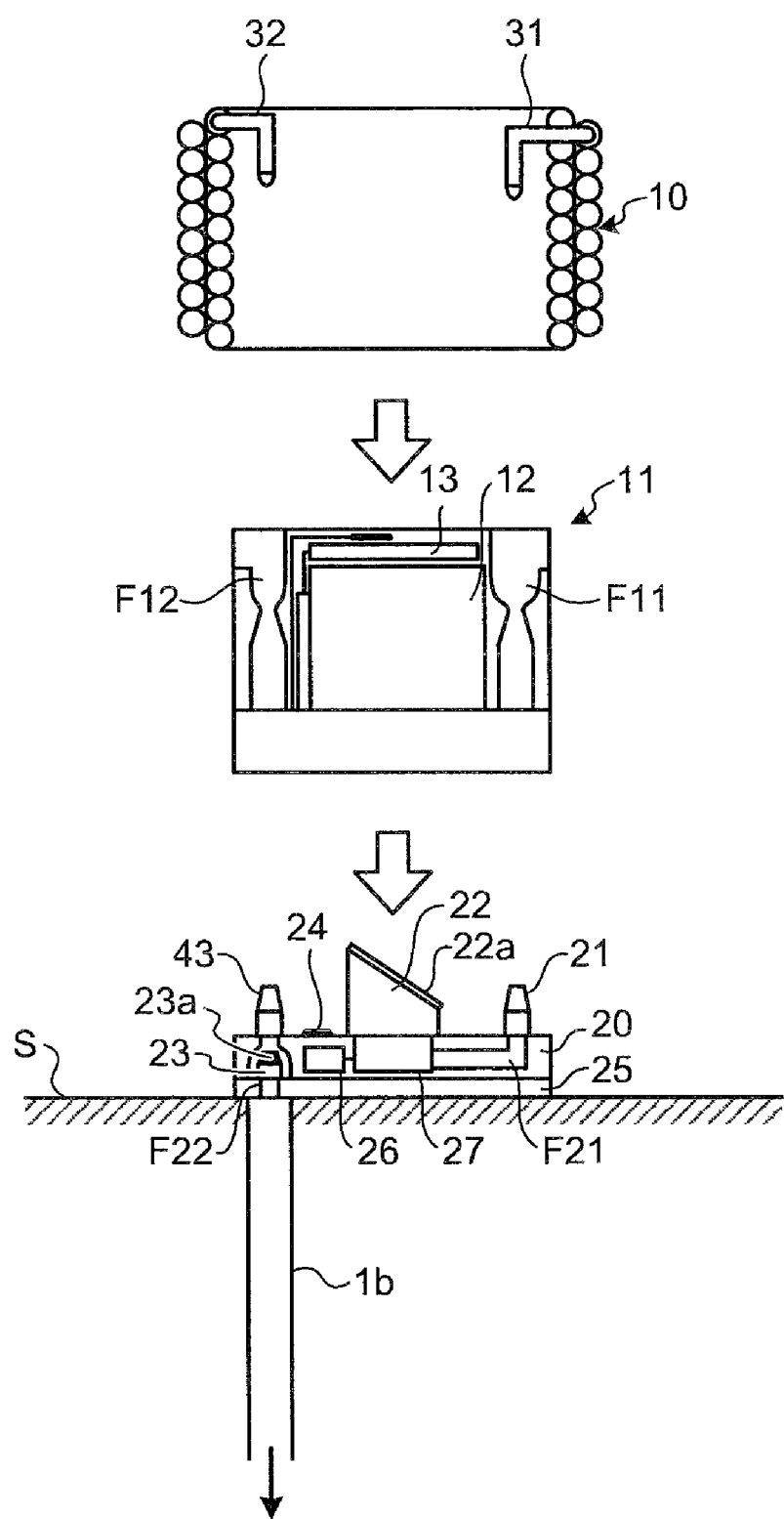
FIG. 10 is an exploded cross-sectional view of the medicinal-solution administration device illustrated in FIG. 8.

FIG. 8 is an exploded perspective view of a medicinal-solution administration device according to the third embodiment of the present invention. FIG. 9 is a cross-sectional view of the medicinal-solution administration device illustrated in FIG. 8. FIG. 10 is an exploded cross-sectional view of the medicinal-solution administration device illustrated in FIG. 8. In FIGS. 8 to 10, the medicinal-solution administration device is formed such that the medicinal-solution connection portion 32 and the drive-liquid connection portion 31 described in the first embodiment are added to the configuration of the second embodiment, and the medicinal-solution reservoir 10 is detachably attached to the drive-liquid unit 11.

In the third embodiment, because the medicinal-solution reservoir 10 and the drive-liquid unit 11 are independently detachable, it is possible to flexibly and easily replace arbitrary consumable supplies.

Figure 11:
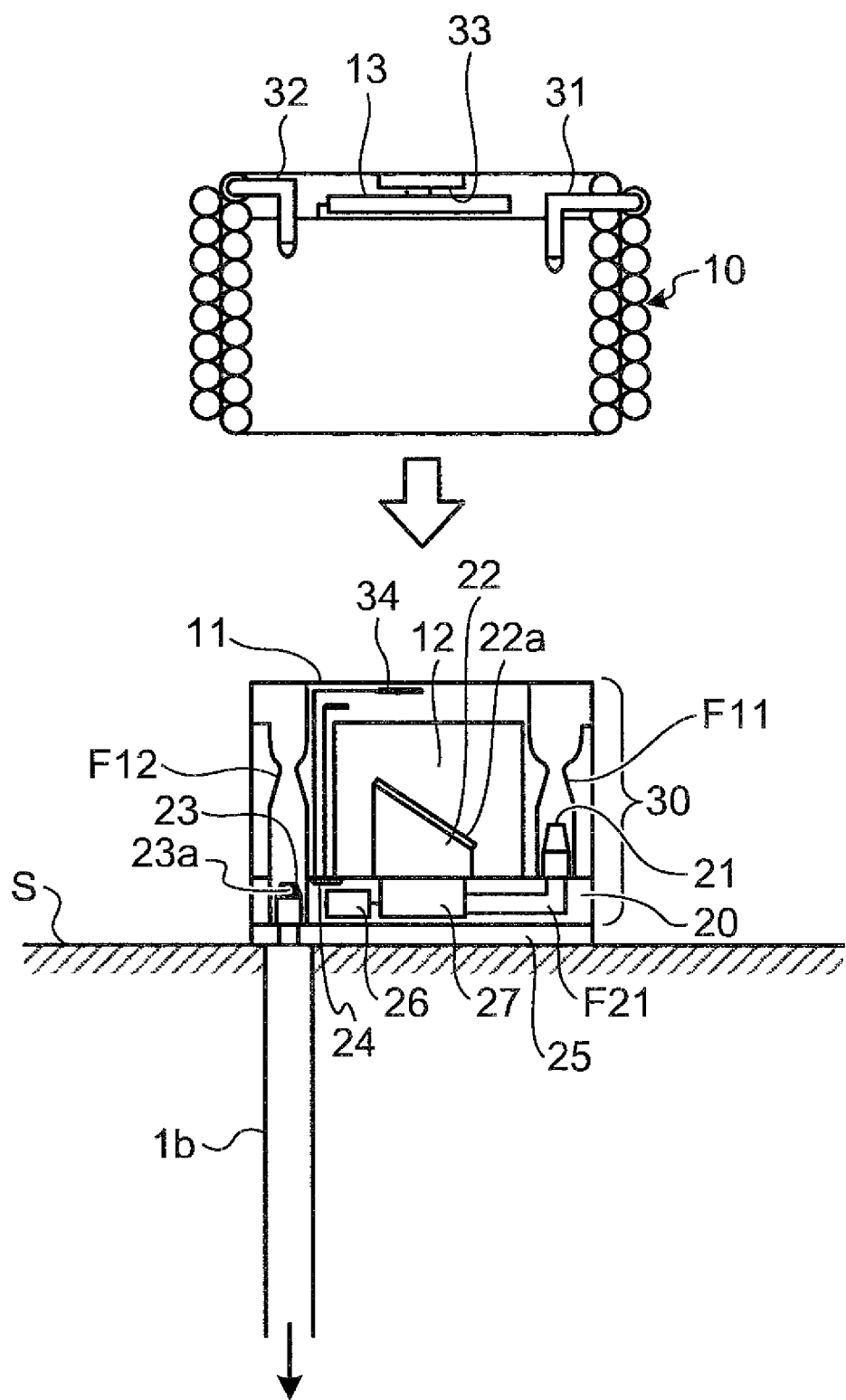
FIG. 11 is an exploded cross-sectional view of a configuration in which a battery is mounted on a medicinal-solution reservoir side.

In the first and the third embodiments described above, the battery 13 is mounted on the drive-liquid unit 11 side; however, it is not limited thereto. It is possible to mount the battery 13 on the medicinal-solution reservoir 10 side as illustrated in FIG. 11. In this configuration, particularly when only the medicinal-solution reservoir 10 is detachable as described in the first embodiment, it is possible to appropriately replace the battery as consumable supplies.

Figure 12:
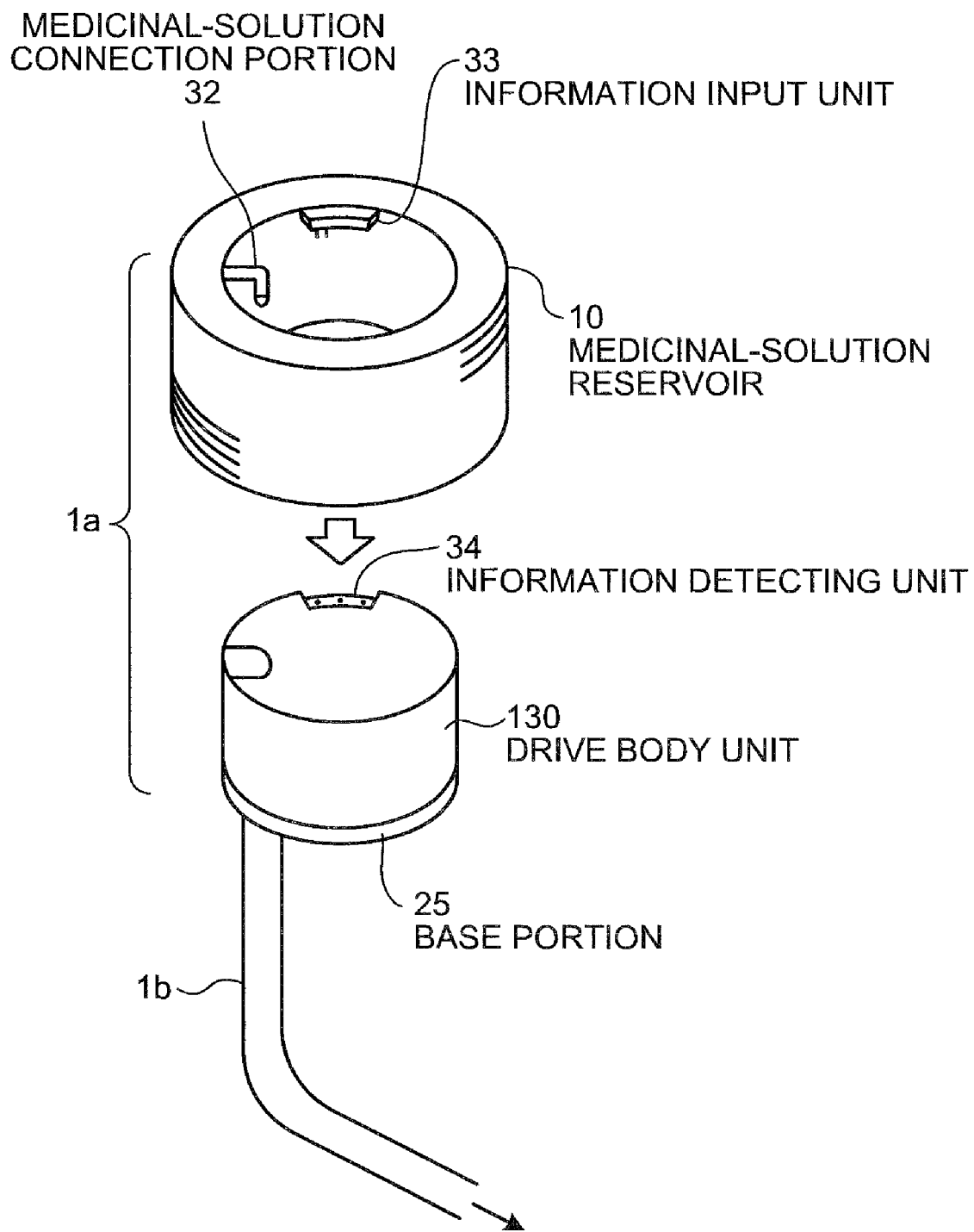
FIG. 12 is an exploded perspective view of a configuration in which a Perista Pump that directly discharges a medicinal solution is used as a driver.

Furthermore, in the first to the third embodiments described above, the electro-osmotic pump is used as an example; however, it is not limited thereto. It is possible to use other types of pumps, e.g., a Perista Pump, as the driver. In this case, because the Perista Pump can directly discharge the medicinal solution, it is possible to omit the drive-liquid unit 11 from the configuration. For example, as illustrated in FIG. 12, it is possible to cause a drive body unit 130 realized by the Perista Pump to discharge the medicinal solution in the detachable medicinal-solution reservoir 10 to the cannula 1b. In this case, the drive body unit (driver) 130 may be configured such that an eccentric cam (drive transmitter) is attached to an axis of a rotary motor (drive generator), and the medicinal-solution reservoir may be configured in a tube structure as a pipeline arranged in a loop shape. In this case, it is possible to realize a mechanism in which the eccentric cam that is driven along with the rotation of the rotary motor pushes to deform the loop-shaped tube from the outside so that the medicinal solution contained in the tube is pushed forward. In this manner, when the driver for driving the medicinal solution is arranged inside the loop of the loop-shaped pipeline in a geometrical arrangement, a compact design can be achieved. The medicinal-solution reservoir may be arranged on portions other than the inside of the driver. For example, the medicinal-solution reservoir may be arranged on the top portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medicinal-solution administration device comprising:
   a body unit, the body unit comprising:
      a cannula for implantation into a body;
      a base portion for placement on an outer surface of the body, the base portion being mateably connected to the cannula;
      a drive generator that generates a drive force, the drive generator disposed on the base portion and equipped with a medicinal-solution receiving portion that is in communication with the cannula; and
   a cartridge unit that is attachable to and detachable from the body unit, the cartridge unit comprising:
      a medicinal-solution reservoir that accommodates at least a medicinal solution and feeds the medicinal solution toward the medicinal-solution receiving portion, the medicinal-solution reservoir comprising a coil-shaped tube having first and second ends,
      a power source that causes the drive generator to drive, and
      a drive transmitter comprising a drive-liquid reservoir capable of accommodating a drive liquid that transmits the drive force generated by the drive generator to the medicinal-solution reservoir to push out the medicinal solution in the medicinal-solution reservoir.

2. The medicinal-solution administration device according to claim 1, wherein
   a one-way valve that prevents back-flow of the medicinal solution is arranged at a receiving port at which the medicinal solution is received and then delivered to an inside of a living body.

3. The medicinal-solution administration device according to claim 1, wherein
   the medicinal-solution reservoir includes an information input unit for inputting medicinal-solution administration information related to an administration amount of the medicinal solution, and
   the drive generator includes a drive control unit that acquires the medicinal-solution administration information and controls discharge of the drive liquid based on the medicinal-solution administration information.

4. The medicinal-solution administration device according to claim 1, wherein the drive generator is equipped with a drive liquid intake portion, a drive liquid discharging portion and the medicinal-solution receiving portion that is communicated with the cannula.

5. The medicinal-solution administration device according to claim 4, wherein the drive liquid intake portion, the drive liquid discharging portion, and the medicinal-solution receiving portion are in communication with the drive-liquid reservoir, the first end of the coil-shaped tube and the second end of the coil-shaped tube, respectively, when the cartridge unit is attached to the body unit.

6. The medicinal-solution administration device according to claim 1, wherein
   the drive generator includes a pump that variably discharges the drive liquid to the medicinal-solution reservoir.

7. The medicinal-solution administration device according to claim 6, wherein the cannula guides the medicinal solution toward a treatment target inside the body.

8. The medicinal-solution administration device according to claim 6, wherein
   the drive-liquid reservoir includes a filter at an intake port thereof through which the drive liquid is taken in.

9. The medicinal-solution administration device according to claim 6, wherein
   the drive transmitter is arranged in an internal space formed by the tube member, at least a portion of which is in the form of either the loop or the coil.

10. The medicinal-solution administration device according to claim 9, wherein
    a base portion of the cannula is arranged in an internal space formed by the medicinal-solution reservoir.

11. The medicinal-solution administration device according to claim 6, wherein
    the drive generator is arranged in an internal space formed by the tube member, at least a portion of which is in the form of either the loop or the coil as the continuous loop.

12. The medicinal-solution administration device according to claim 11, wherein
    a base portion of the cannula is arranged in an internal space formed by the medicinal-solution reservoir.

* * * * *